(12) United States Patent
Kamihara et al.

(10) Patent No.: US 9,310,388 B2
(45) Date of Patent: Apr. 12, 2016

(54) AUTOMATIC ANALYZER AND ANALYSIS METHOD

(75) Inventors: Kumiko Kamihara, Mito (JP); Satoshi Mitsuyama, Tokyo (JP); Tomonori Mimura, Kasama (JP); Chihiro Manri, Kawagoe (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 904 days.

(21) Appl. No.: 13/318,535

(22) PCT Filed: Apr. 12, 2010

(86) PCT No.: PCT/JP2010/002631
§ 371 (c)(1),
(2), (4) Date: Nov. 30, 2011

(87) PCT Pub. No.: WO2010/128575
PCT Pub. Date: Nov. 11, 2010

(65) Prior Publication Data
US 2012/0109534 A1     May 3, 2012

(30) Foreign Application Priority Data
May 8, 2009 (JP) .................................. 2009-113138

(51) Int. Cl.
*G01C 19/00*     (2013.01)
*G01N 35/00*     (2006.01)
*G01N 21/27*     (2006.01)

(52) U.S. Cl.
CPC ........ *G01N 35/00603* (2013.01); *G01N 21/272* (2013.01)

(58) Field of Classification Search
CPC ................. G01N 35/00613; G01N 2035/0097
USPC ..................................................... 702/104, 19
See application file for complete search history.

(56) References Cited

U.S. PATENT DOCUMENTS

2007/0178504 A1*   8/2007   Colpitts et al. .................... 435/6
2008/0133141 A1*   6/2008   Frost .............................. 702/19
(Continued)

FOREIGN PATENT DOCUMENTS

JP     57-147039 A     9/1982
JP     6-194313     *     7/1994
(Continued)

OTHER PUBLICATIONS

Y. Yamamoto, Detection of the Abnormality that Originates from the Reaction System that used the Reaction Time Course, Japanese Journal of Clinical Laboratory Automation, vol. 34, No. 2, Apr. 1, 2009, pp. 163-169.

*Primary Examiner* — Mischita Henson
*Assistant Examiner* — Stephanie Bloss
(74) *Attorney, Agent, or Firm* — Mattingly & Malur, PC

(57) ABSTRACT

In known automatic analyzers for detecting an abnormality by approximating reaction process data using a function, accuracy of detecting a reaction abnormality is degraded because of poor approximation accuracy depending on test items. Data processing means stores the absorbance and time of day at which the absorbance is measured as time-series data. Letting x denote absorbance, t denote time, and * denote a symbol representing multiplication, we have a function $x=a0+a1*\exp(-k1*t)+a2*\exp(-k2*t)$. Values of parameters a0, a1, a2, ai, k1, and k2 are calculated so that a difference between the absorbance at the measured time calculated using the above expression and the time-series data is minimal, and presence of an abnormality is determined based on the parameter values.

10 Claims, 10 Drawing Sheets

(56) References Cited

U.S. PATENT DOCUMENTS

2009/0040517 A1* 2/2009 Maier et al. .................. 356/301
2010/0099194 A1* 4/2010 Okabayashi .................. 436/55

FOREIGN PATENT DOCUMENTS

| | | | | |
|---|---|---|---|---|
| JP | 6-194313 A | 7/1994 | | |
| JP | 6-249856 | * 9/1994 | ............ | G01N 35/00 |
| JP | 8-219984 A | 8/1996 | | |
| JP | 2003-57248 A | 2/2003 | | |
| JP | 2004-347385 A | 12/2004 | | |
| JP | 2006-337125 A | 12/2006 | | |
| JP | 2009-47638 A | 3/2009 | | |
| JP | 2009-047638 | * 5/2009 | ............ | G01N 35/00 |

* cited by examiner

AUTOMATIC ANALYZER AND ANALYSIS METHOD

TECHNICAL FIELD

The present invention relates to automatic analyzers that perform a qualitative/quantitative analysis of a biological sample such as blood and urine, and analysis methods, and more particularly to an automatic analyzer that includes a mechanism for measuring changes with time in measured values, and an analysis method.

BACKGROUND ART

An automatic analyzer for clinical tests dispenses predetermined amounts of a reagent and a sample for subsequent mixing and reaction. Absorbance of a reaction solution is then measured for a predetermined period of time and, based on measurements, concentration and activity values of substances to be measured are found.

Analyses for clinical tests require, in addition to an analyzer, a reagent for each analysis item, a standard solution for reagent calibration, an apparatus currently making an analysis, and a quality control sample to be measured for reagent status check. Combination of all these items but the analyzer achieves final analytical performance.

Internal factors of the analyzer directly affecting the analytical performance include, but are not limited to, a sampling mechanism, a reagent dispensing mechanism, a mixing mechanism, an optical system, a reaction vessel, and a thermostat. Factors other than an apparatus such as the automatic analyzer include a reagent, a sample, and liquidity of a control specimen.

In a case where the automatic analyzer is to be used on a daily basis, the foregoing factors need to be checked to thereby determine whether a normal clinical test can be made. Factors may, for example, be checked as follows.

(1) Calibration Using a Standard Solution

A reagent bottle for each item is calibrated. A blank solution and a standard solution are measured to thereby determine an origin and calculate absorbance per unit concentration and a conversion factor (hereinafter referred to as a K factor). In general, a clinical laboratory technologist determines the magnitude of absorbance and time-dependent variations in the K factor to determine whether the results of calibration are acceptable.

(2) Quality Control

A quality control sample with a known concentration is measured after the calibration to check for any difference from a reference value. If a patient specimen is being measured, the quality control sample is measured regularly at predetermined time intervals to thereby check for any deviation from a permissible value. If the permissible value is exceeded, an inspection is made on the assumption that something is wrong with either the reagent or analyzer.

In daily tests, data is checked using reaction process data. The prozone check is known for detecting abnormality in data in measurement in an endpoint method. With reagents used in the immunoturbidimetric method for measuring IgA (immunoglobulin A), CRP (C-reactive protein) and the like, protein may deposit as a precipitate as affected by salt concentration of reagent compositions. The precipitate may subject the reaction process to fluctuations that very often occur actually in a latter part of a reaction time. The fluctuations occurring at a photometric point used for calculation of concentration hampers accurate measurement. An antigen re-addition method and a reaction rate ratio method are available as methods for checking this. In either method, an alarm is issued to notify that a limit value specified with a parameter is exceeded.

Methods as disclosed, for example, in patent documents 1 and 2 are known as methods for determining whether there is an abnormality by using the reaction process data (time-series data of absorbance). In the method of patent document 1, reference time-series data is generated in advance using a chemical reaction model and stored in memory; reaction process data of the sample is then compared with the reference time-series data; the method determines that there is an abnormality when there is large deviation. The method of patent document 2 approximates a change in absorbance by using a function previously stored in memory and determines an abnormality based on the magnitude of deviation of actually measured absorbance from the absorbance calculated, in which the absorbance change thereof is approximated with the function.

PRIOR ART DOCUMENTS

Patent Documents

Patent Document 1: JP-2004-347385-A
Patent Document 2: JP-2006-337125-A

SUMMARY OF THE INVENTION

Problem to be Solved by the Invention

Improvements made in performance of the automatic analyzer in recent years have enabled accurate analysis of various items even with slight amounts of samples and reagents. On the contrary, however, accurate analysis may be hampered by even a slight abnormality in an analyzer or apparatus component or a slight change in quality of the specimen or reagent. Automatic analyzers for clinical test measure, at predetermined time intervals, absorbance of a solution in which a sample is reacted with a reagent, and determine an absorbance change rate and final absorbance from the measured time-series data of absorbance. The data thus obtained is used to calculate concentration and enzyme activity values of substances to be measured. During monitoring of a reaction process, the automatic analyzer performs sampling, reagent dispensing, and mixing processes. These processes entail a plurality of error factors. So far, in particular, a quantitative evaluation has not been possible of performance or a level of the mixing process. Further, for want of criteria for determination, only a vague evaluation has been made in terms of, for example, a level of reproducibility and whether there is a careless mistake (as indicated by discontinuous measured values or other measured values that obviously reveal evidence of some abnormality). For any factor directly affecting the reaction, for example, if a reagent is diluted with water for rinsing a reagent probe or if a user inadvertently mixes an irrelevant solution with the reagent, the automatic analyzer needs to detect such an abnormality, inform the user of the abnormality, and prompt him or her to re-check or service the apparatus.

It is difficult for a laboratory technologist, the user of the automatic analyzer, to check visually all of the reaction processes in his or her daily test routine. Especially when a measured value falls within a normal value range, he or she tends to overlook reaction abnormalities and may yield low-accuracy results.

Patent document 1 discloses the expression shown below as a chemical reaction model. Where, t denotes time of day, x denotes absorbance, and A0, A1, and k denote parameters.

$$x(t)=A0+A1\exp(-kt) \quad \text{(Expression 1)}$$

Patent document 2 discloses the expressions shown below, in addition to (expression 1), as functions that approximate a change in the absorbance. Where, t denotes time of day, x denotes absorbance, and A, B, and k denote parameters.

$$x=-kt+B \quad \text{(Expression 2)}$$

$$x=A/(1+kt)+B \quad \text{(Expression 3)}$$

Depending on the combination of the measurement item and the reagent, however, the functions of the above-referenced (expression 1) to (expression 3) may not be able to approximate accurately the change with time in the absorbance to be measured, which poses a problem in that abnormalities cannot be accurately detected.

FIG. 3 shows an example of reaction process data (absorbance time-series data) for one item (TG or neutral fat) of a biochemical test and corresponding reaction process data approximated with (expression 1). An abscissa 110 represents time elapsed, while an ordinate 120 represents the absorbance. A symbol 140 represents an absorbance value actually measured at each point in time and a curve 150 represents the reaction process data approximated with (expression 1). In this example, (expression 1) accurately approximates the actual reaction process data. Meanwhile, FIG. 4 shows another example of reaction process data for another test item (TP or total protein) approximated with (expression 1), showing that absorbance values calculated with the approximate expression are lower than actual absorbance at points in time of 5 to 10, higher at points in time of 10 to 27, and lower at points in time of 27 onward, thus revealing that approximation accuracy is poor. In addition, FIG. 5 shows results of approximation made of the same data using (expression 3). Though (expression 3) approximates better than (expression 1), an error is large at a starting point of approximation and the absorbance values calculated with the approximate expression are lower than actual absorbance at points in time of 7 to 15. The situation can be more noticeably observed by plotting errors between the absorbance values calculated with the approximate expression and actual absorbance measurements. FIG. 6 shows errors when (expression 1) is used and errors when (expression 3) is used. An abscissa 220 represents errors. A dash-single dot line 230 represents errors of approximation made using (expression 1) at different points in time and a broken line 240 represents errors of approximation made using (expression 3).

Causes of these errors lie in nature of a chemical reaction occurring in a reaction vessel regardless of whether the analysis is made by endpoint method. For a reaction process of an item, in which chemical reactions of two or more different types occur sequentially at rates close to each other, approximation is difficult with only one type of chemical reaction formula. With TP that has been shown earlier as an example of difficult approximation, it is well-known that, though the reaction is simple in which protein in the sample reacts with biuret reagent to show a blue color, the rate of reaction with the biuret reagent varies depending on the type of protein contained in the TP (mostly, albumin and globulin), so that varying reactivity with the reagent results for a sample with the same TP concentration depending on content of albumin and globulin in the sample. When reaction of a sample is evaluated based on its reactivity with a reagent, therefore, the method of patent document 1 having only one parameter for reactivity fails to offer accurate approximation and is thus insufficient for an evaluation factor for detecting reaction abnormalities.

The methods disclosed in patent documents 1 and 2 compare photometric data readings at different points in time with values calculated by approximate function to find square errors over an entire photometric time, and determine abnormalities using the square errors. The magnitude of deviation between the measured data and the approximated data may therefore be known; however, it is difficult to determine a pattern of deviation (whether the deviation depends on time, and whether the measured data is greater or smaller than the approximated value), which makes it difficult to estimate a cause of the deviation.

Means for Solving the Problem

An arrangement of the present invention for solving the problem is as described below.

An automatic analyzer includes: a storage mechanism for storing approximate expressions for a change in a measured value with time, each of the approximate expression being associated with a corresponding test item or specimen; a parameter optimizing mechanism for optimizing a parameter of the approximate expressions stored in the storage mechanism so as to be associated with an actually measured value; and a determining mechanism for determining presence of an abnormality based on the parameter optimized by the parameter optimizing mechanism.

The storage mechanism stores information and may be any mechanism as long as the mechanism can store information. Examples include, but are not limited to, a semiconductor memory, a hard disk storage device, a floppy (a registered trademark) disk storage device, and an optical magnetic storage device. The storage mechanism is typically disposed inside a cabinet of a control computer, but may be an independent mechanism. The parameter optimizing mechanism determines each of multiple parameters of an approximate expression using a parameter fitting algorithm, such as the least squares method, so that the parameter best fits actual data. The parameter optimizing mechanism is typically formed of software built into a control computer or a dedicated computer and hardware for operating the software. The parameter optimizing mechanism may nonetheless be a mechanism of any mode, as long as the mechanism can determine parameters through parameter fitting.

The determining mechanism determines whether the reaction involves an abnormality or obtains proof that the reaction is terminated normally based on the parameter determined by the parameter optimizing mechanism, through a comparison with a threshold value or a multivariate analysis, for example, such techniques as the Mahalanobis-Taguchi method and a neural network. The determining mechanism is typically formed of software built into a control computer or a dedicated computer and hardware for operating the software. The determining mechanism may nonetheless be a mechanism of any mode, as long as the mechanism can determine whether an abnormality exists or obtain proof that the reaction is terminated normally based on a parameter.

A preferred embodiment of the present invention will be described below.

The present invention prepares, from reaction process data, a plurality of approximate expressions that accurately fit a circular curve of an endpoint method and selects in advance a highly accurate approximate expression for each item or specimen. A parameter (e.g., a coefficient, an intercept of the approximate expression) that matches well with measured data is then calculated for the selected approximate expression and whether or not a proper reaction is made is determined based on deviation of numeric values of a plurality parameters obtained therefrom from values they should be. For example, apparatus abnormality, reagent deterioration, and quality control may be determined continuously and for each individual test.

The plurality of approximate expressions may, for example, be as follows.

$$x = a_0 + a_1 * \exp(-k_1 * t) + a_2 * \exp(-k_2 * t) \quad \text{(Expression 4)}$$

$$x = a_0 + \Sigma\{ai * \exp(-ki * t)\} \quad \text{(Expression 5)}$$

$$x = a_0 + \Sigma[n]\{ai * \exp(-ki * t)\} + \Sigma[m]\{bi/(ci + di * t)\} + \Sigma[l]\{(pi/(\exp(qi * t) + ri))\} \quad \text{(Expression 6)}$$

The problem can be solved as follows. Specifically, values of parameters $a_0$, $a_1$, $a_2$, ai, $k_1$, $k_2$, ki, bi, ci, di, pi, qi, and ri in the expressions cited above are calculated such that a difference between the measured value of absorbance at a measuring point in time and the time-series data obtained with the approximate expression is small. It is then determined whether there is an abnormality based on the values of the parameters. In the expressions, t is a measuring point in time of the absorbance, x is the absorbance, * is a symbol representing multiplication, $\Sigma\{\ \}$ is a symbol representing a sum of all values obtained by substituting i in $\{\ \}$ for a value of 1 to n, $\Sigma[n]\{\ \}$ is a symbol representing a sum of all values, each value being obtained by substituting i in $\{\ \}$ for a value of 1 to n, $\Sigma[m]\{\ \}$ is a symbol representing a sum of all values, each value being obtained by substituting i in $\{\ \}$ for a value of 1 to m, $\Sigma[l]\{\ \}$ is a symbol representing a sum of all values, each value being obtained by substituting i in $\{\ \}$ for a value of 1 to l, and n, m, and l are each whole numbers more than 1.

The automatic analyzer having arrangements as described above permits accurate approximation and even more accurate determination of abnormalities even in test items for which accurate approximation has been difficult with functions. In addition, since abnormalities are determined based on, not the difference between the absorbance obtained as a result of approximation and actual absorbance measurements, but a value of a parameter included in the approximate expression, specific deviation relative to correct data can be easily identified. Further, a comparison with a theoretical formula of reaction kinetics facilitates estimation of possible causes of abnormalities.

Effects of the Invention

The automatic analyzer and the analysis method of the present invention allow abnormalities of the analyzer and the apparatus to be checked from daily routine test data in a greater number of test items than the related art. This contributes to maintenance of performance of the analyzer and apparatus.

When a mixing mechanism develops an abnormality, the reaction rate changes relative to that under normal conditions. In a specimen with a known concentration, such as a control specimen and a standard solution, monitoring parameters relating to the reaction rate among other approximate function parameters is to check performance of the mixing mechanism over time. This allows the automatic analyzer to actively notify the user of necessity for servicing or replacement of the mixing mechanism. Performance or level of mixing, evaluation of which has been vague, can thus be quantified, which allows abnormalities of the mixing mechanism to be detected and an optimum parameter for each reagent to be verified and determined.

The reaction rate is affected, if, for example, the reagent is deteriorated or diluted with rinsing water in a reagent probe. Since the present invention quantifies a sluggish pace of reaction, reaction abnormalities can be detected. Evaluation of performance of the reagent can thus be made and reagent deterioration caused by a human mistake during a daily routine test can be detected, so that an erroneous data output can be prevented from being overlooked.

In addition, use of the reaction process data permits evaluation of each individual measured specimen, which serves as new evaluation criteria that give measurements of each specimen credibility which has been impossible with the related art evaluation method. Moreover, parameter distributions are sorted into normal and abnormal ones in advance. This allows measurements of general specimens suggesting parameters that belong to the normal distribution to be guaranteed with quantitative evaluation criteria. If the measurements are guaranteed, need for re-test may be eliminated for test results that do not agree with the preceding values or test results of panic values.

MODE FOR CARRYING OUT THE INVENTION

Embodiments of the present invention will be described below with reference to the accompanying drawings.

First Embodiment

Figure 2:
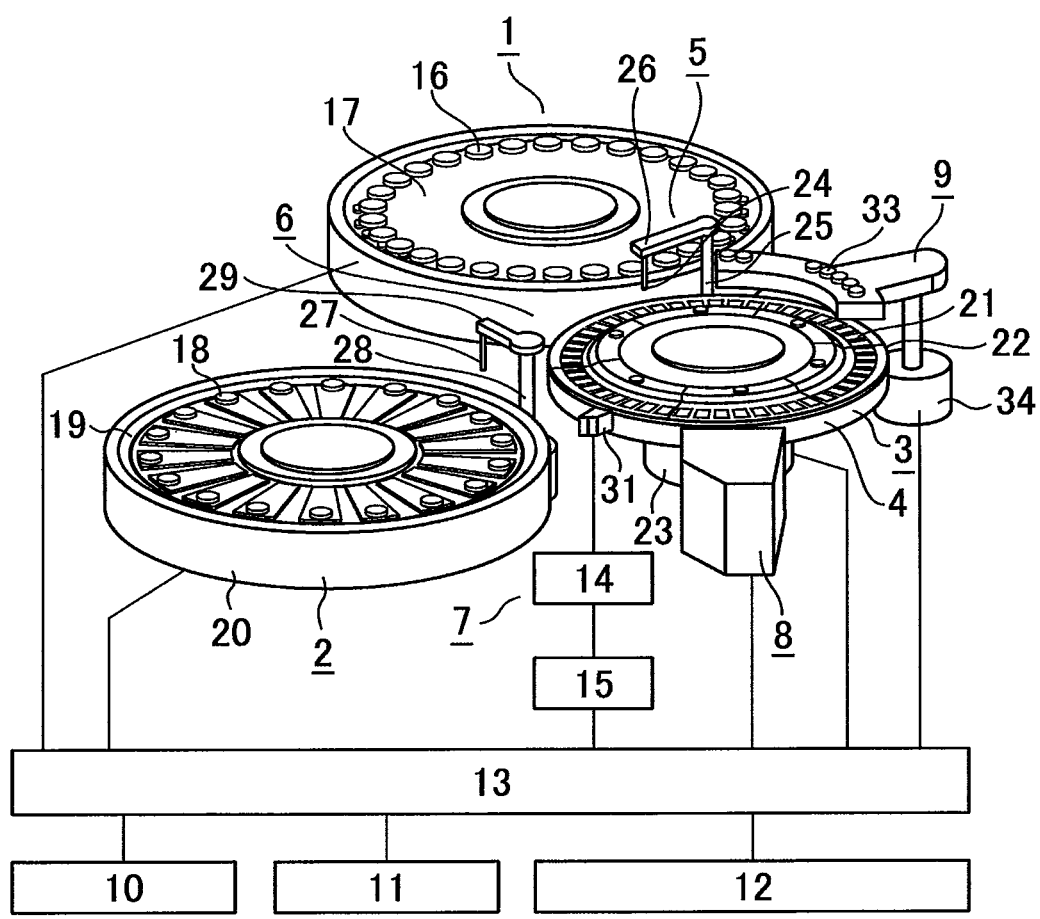
FIG. 2 is an illustration showing schematically arrangements of an automatic analyzer to which the present invention is applied.
Figure 3:
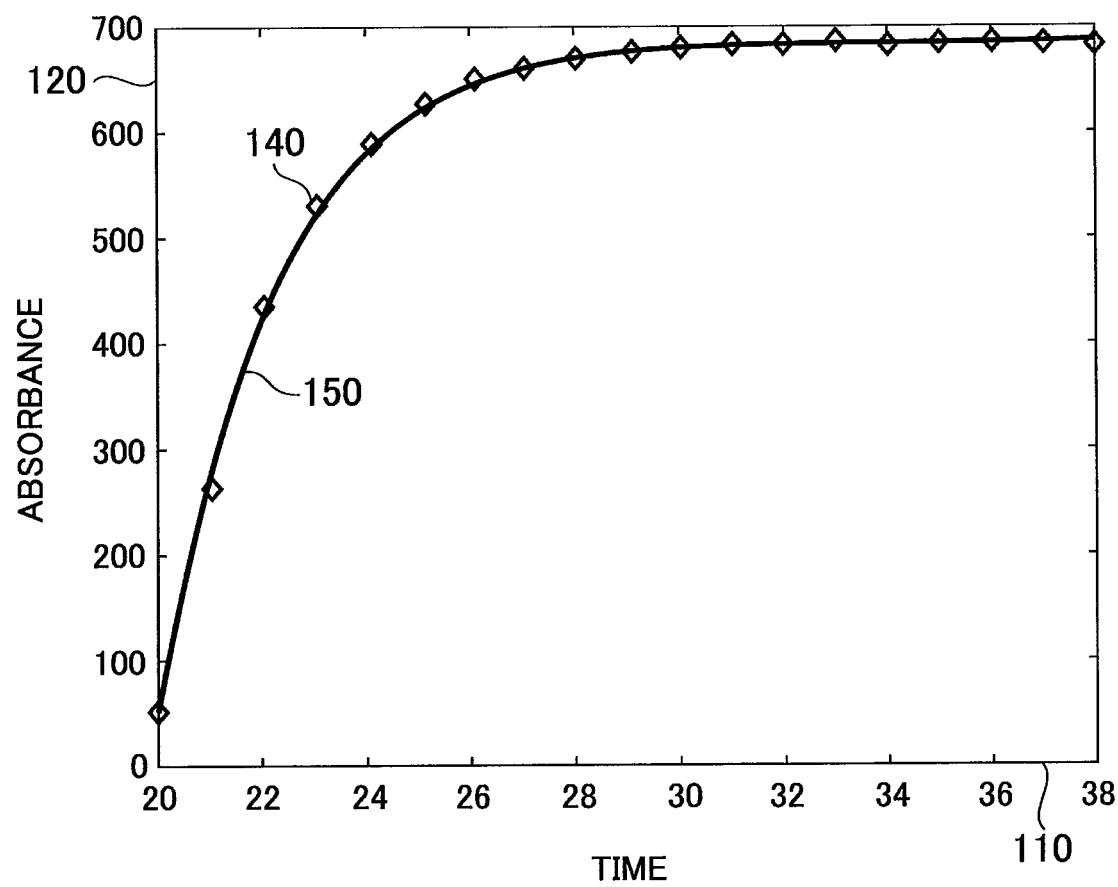
FIG. 3 is a graph showing an example of changes with time in absorbance measurements and absorbance calculated with an approximate expression.

An automatic analyzer according to a first embodiment of the present invention will be described in detail below. FIG. 2 is an illustration showing schematically arrangements of a biochemical automatic analyzer to which the present invention is applied, wherein reference numeral 1 denotes a sample disk, reference numeral 2 denotes a reagent disk, reference numeral 3 denotes a reaction disk, reference numeral 4 denotes a reaction tank, reference numeral 5 denotes a sampling mechanism, reference numeral 6 denotes a pipetting mechanism, reference numeral 7 denotes a mixing mechanism, reference numeral 8 denotes a photometry mechanism, reference numeral 9 denotes a rinsing mechanism, reference numeral 10 denotes a display section, reference numeral 11 denotes an input section, reference numeral 12 denotes a storage section, reference numeral 13 denotes a control section, reference numeral 14 denotes a piezoelectric element driver, reference numeral 15 denotes a mixing mechanism controller, reference numeral 16 denotes a sample vessel, reference numerals 17, 19 denote circular disks, reference numeral 18 denotes a reagent bottle, reference numeral 20 denotes a cool box, reference numeral 21 denotes a reaction vessel, reference numeral 22 denotes a reaction vessel holder, reference numeral 23 denotes a drive mechanism, reference numerals 24, 27 denote probes, reference numerals 25, 28 denote bearing shafts, reference numerals 26, 29 denote arms, reference numeral 31 denotes a fixing section, reference numeral 32 denotes an electrode, reference numeral 33 denotes a nozzle, and reference numeral 34 denotes a vertical drive mechanism. The storage section stores, for example, analysis parameters, number of analyses to be made by each reagent bottle, maximum number of analyses to be made, calibration results, and analyses. The sample is analyzed in the following sequence as detailed below: sampling, dispensing reagent, mixing, photometric measurement, rinsing reaction vessel, and converting concentration and other data processing operations.

The control section 13 controls the sample disk 1 via the display section 10. A plurality of sample vessels 16 are arranged on a circular on the sample disk 1, being moved to a position beneath the sampling probe 24 according to an order of samples to be analyzed. A predetermined amount of specimen in the specific sample vessel 16 is dispensed into the reaction vessel 21 by a sample pump connected to the specimen sampling mechanism 5.

The reaction vessel 21 into which the sample is dispensed moves to a first reagent adding position in the reaction tank 4. A predetermined amount of reagent picked up from the reagent vessel 18 is added to the moved reaction vessel 21 by a reagent pump (not shown) connected to the reagent dispensing probe 6. The reaction vessel 21 into which the first reagent is added moves to a position of the mixing mechanism 7 at which first mixing is performed. Such operations of adding and mixing the reagent are performed for each of first to fourth reagents.

The reaction vessel 21 in which contents are mixed passes through a flux of light emitted from a light source, so that the photometry mechanism 8 of a multiwavelength photometer detects absorbance prevailing at that time. A signal representing the detected absorbance enters the control section 13 and is converted to corresponding concentration of the specimen. The control section 13 simultaneously determines an abnormality based on the absorbance.

The data obtained through conversion to concentration is stored in the storage section 12 and displayed on the display section. The reaction vessel 21 that has undergone the photometric measurement is moved to the rinsing mechanism 9, rinsed, and served for a subsequent analysis.

Figure 1:
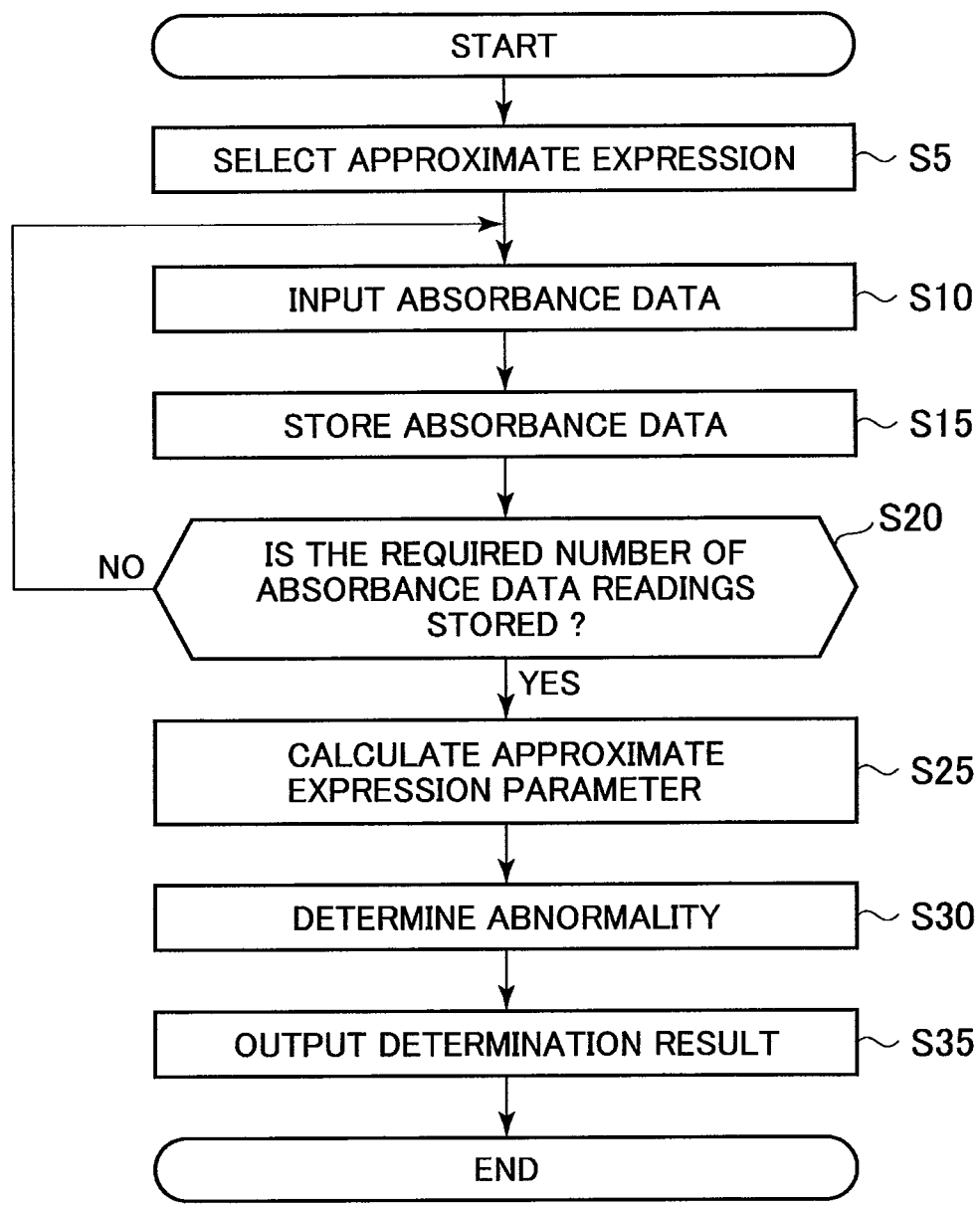
FIG. 1 is a flow chart showing processes performed according to a first embodiment of the present invention.

Processes for determining an abnormality based on the absorbance in the control section 13 will be described in detail below with reference to FIG. 1. FIG. 1 is a flow chart showing processes performed by portions involved in abnormality determination in the control section 13. At the same time that measurement of a test item is started for a specimen, an approximate expression associated with the test item is selected in step S5 from among a plurality of approximate expressions representing changes in absorbance with time.

For the approximate expressions, functions given in (expression 1) to (expression 6), for example, are stored, while the approximate expression most suitable for each test item is stored as a table. This table is then used to select the approximate expression associated with the test item.

The absorbance is measured a plurality of times as time elapses. In step S10, a measured value or an average value of a plurality of measurements taken of the absorbance data is input from the photometry mechanism 8. In a measuring system that uses light with two wavelengths, one with a wavelength (main wavelength) with which the absorbance varies greatly according to a change in tone involved in reaction between the reagent and the specimen and the other with a wavelength (sub-wavelength) with which the absorbance changes little, a difference between absorbance of the main wavelength light and absorbance of the sub-wavelength light is input as the absorbance data. In step S15, the input absorbance data is stored. In step S20, it is determined whether the number of absorbance data readings required for the subsequent processes is stored. When it is determined that the required number of readings is yet to be stored, control is returned back to S10. Input and storage of the absorbance data readings are repeated until the required number of readings is stored. When the required number of readings is stored, control is passed onto step S25.

In step S25, values of parameters in the expression are calculated so that a change with time in the absorbance expressed by the approximate expression selected in step S5 and a change with time in actual absorbance are minimal. Specifically, in step S20, the parameter values in the expression are established so that a square error between the measured and stored absorbance data and the absorbance, calculated using the approximate expression, at the same point in time as that at which the absorbance is measured is as small as feasible. A known least squares calculation method may be employed for calculating the parameter value. A method that may be applied to expressions of various formats, for example, the steepest descent method, may be employed to calculate the parameter value that results in the square error being the smallest. In a reaction in which a plurality of reagents is used, a large change in absorbance begins after a reagent (typically, a final reagent) causing a major change in absorbance is applied. In this case, only data after the reagent causing the major change in absorbance is applied is used for calculating the parameter value.

Figure 4:
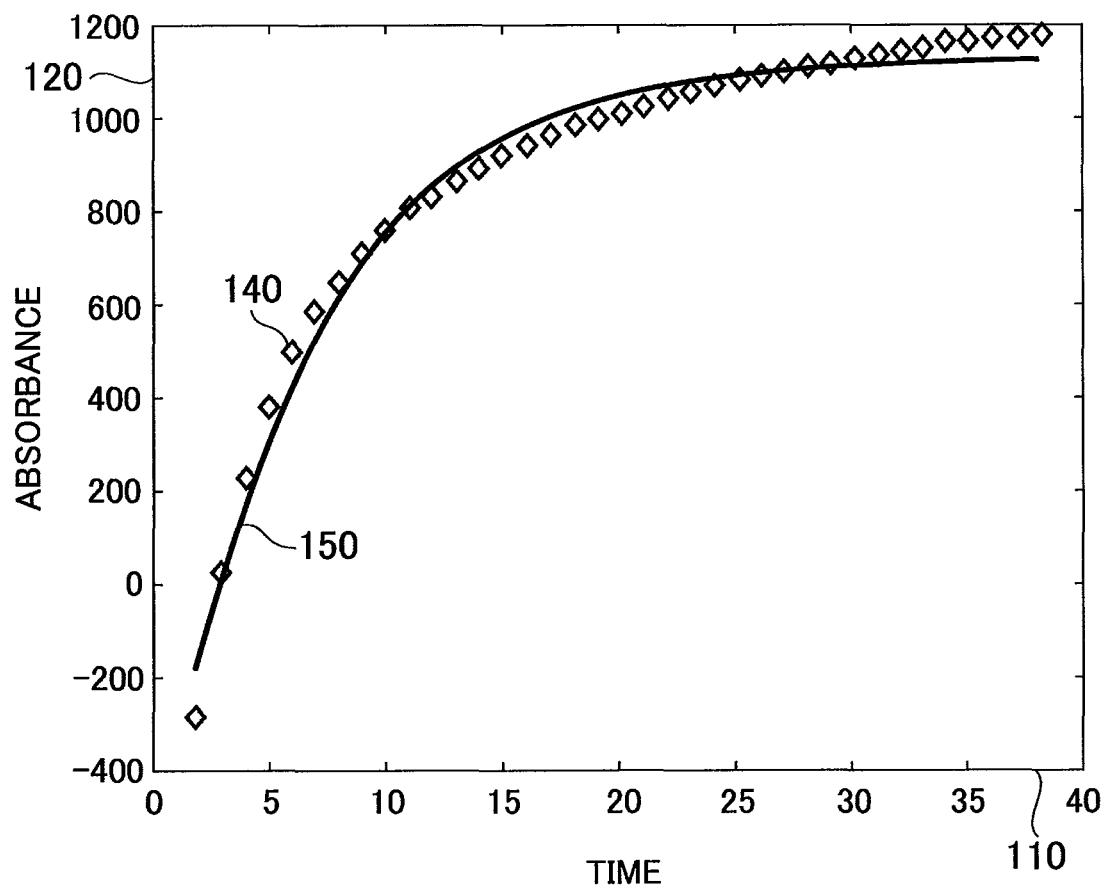
FIG. 4 is a graph showing an example of changes with time in absorbance measurements and absorbance calculated with an approximate expression.
Figure 5:
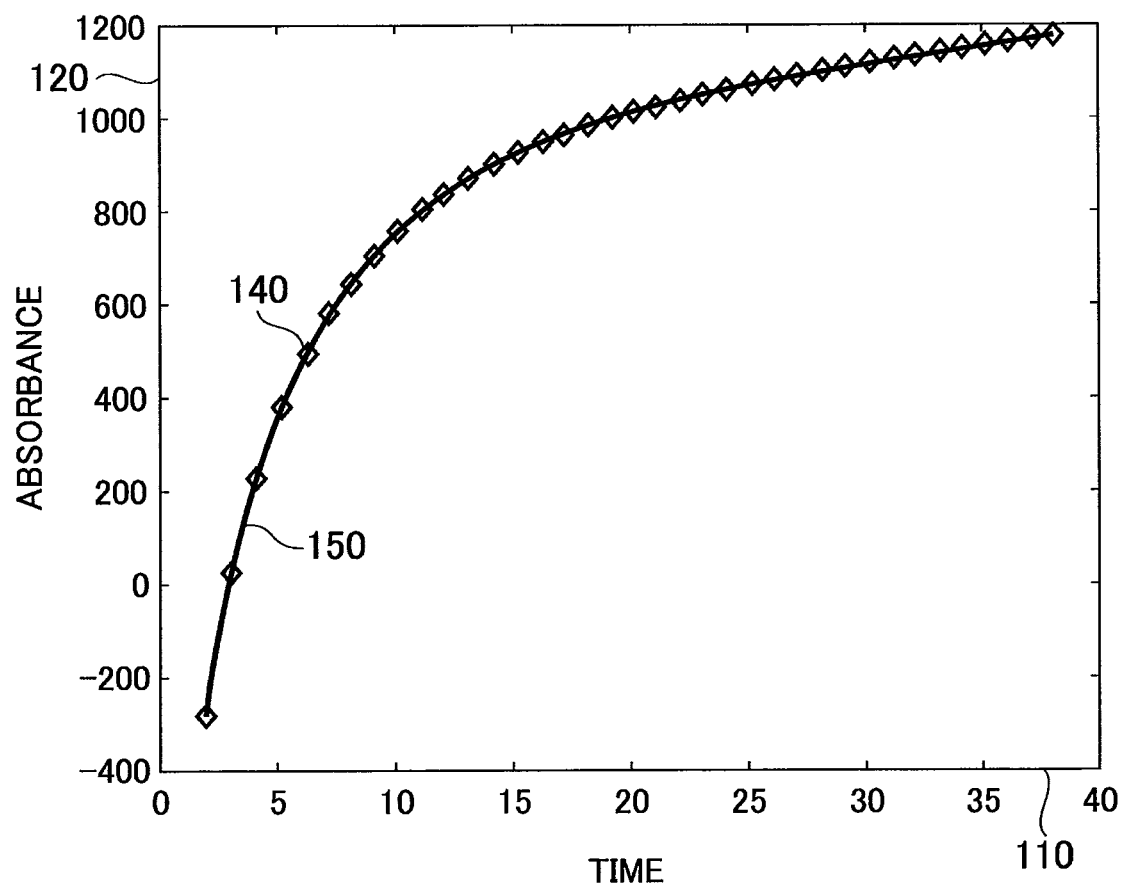
FIG. 5 is a graph showing an example of changes with time in absorbance measurements and absorbance calculated with an approximate expression.
Figure 6:
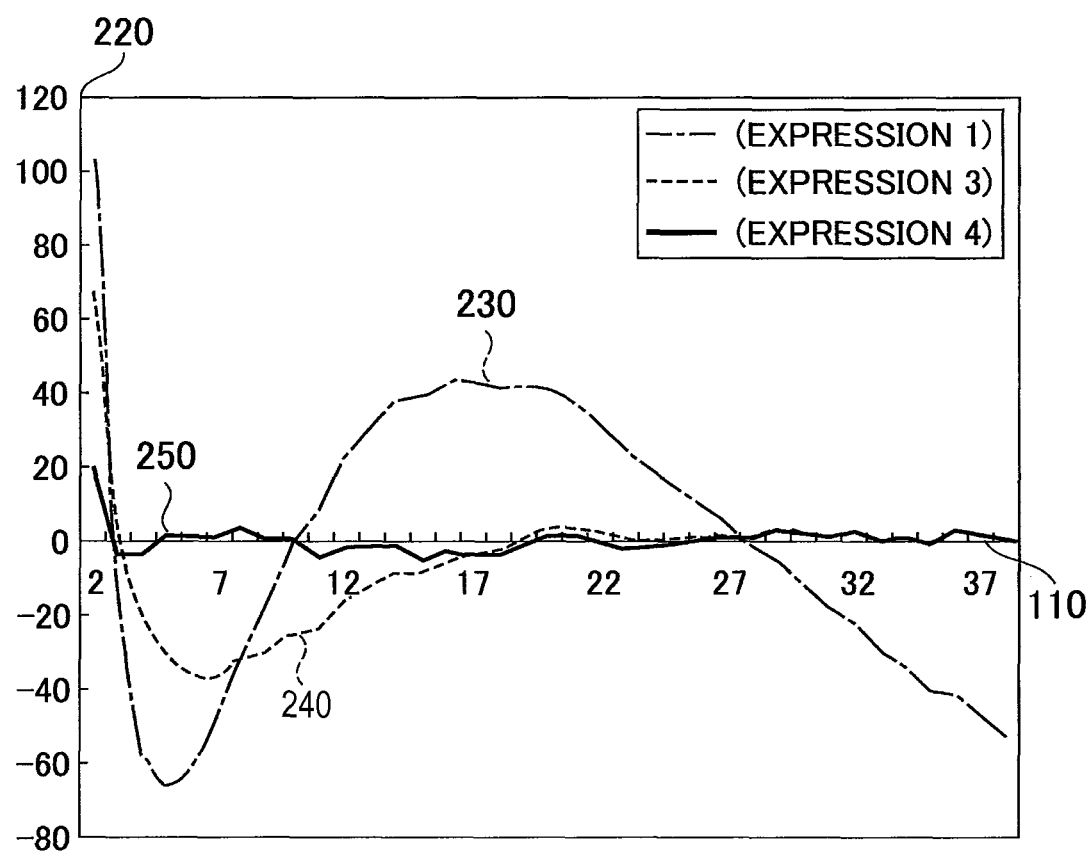
FIG. 6 is a graph showing an example of errors in absorbance measurements and absorbance calculated with an approximate expression.
Figure 7:
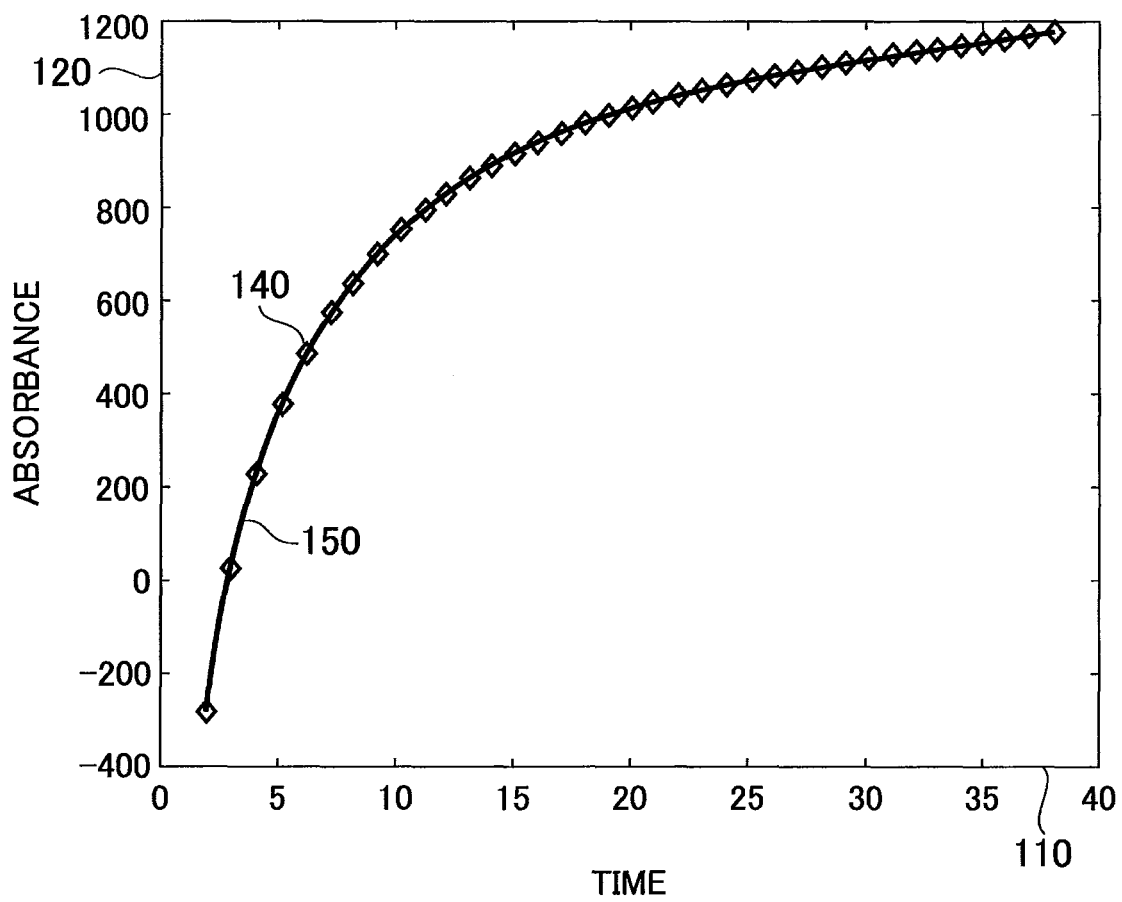
FIG. 7 is a graph showing an example of changes with time in absorbance measurements and absorbance calculated with an approximate expression.

When abnormalities are to be detected according to the present invention, the difference between the absorbance calculated using the approximate expression and the actually measured absorbance needs to be sufficiently small in step 25 for normal data. It is, however, difficult as shown in FIGS. 4 and 5 for the approximate expression used in the related art to establish parameters that result in the difference between the normal data and the absorbance calculated using the approximate expression being sufficiently small. The present invention, however, allows functions of various formats shown in (expression 1) to (expression 6) to be selected in step S5. This allows favorable approximation results to be obtained even with data as shown in FIGS. 4 and 5 with which accurate approximation is difficult in the related art. For example, FIG. 7 is a graph that shows results of approximation made using (expression 4) for the same type of data as the absorbance data shown in FIGS. 4 and 5. A solid line 250 in FIG. 6 represents an error of approximation made using (expression 4). It is known that the error can be considerably minimized as compared with the related art using (expression 1) and (expression 3).

Figure 8:
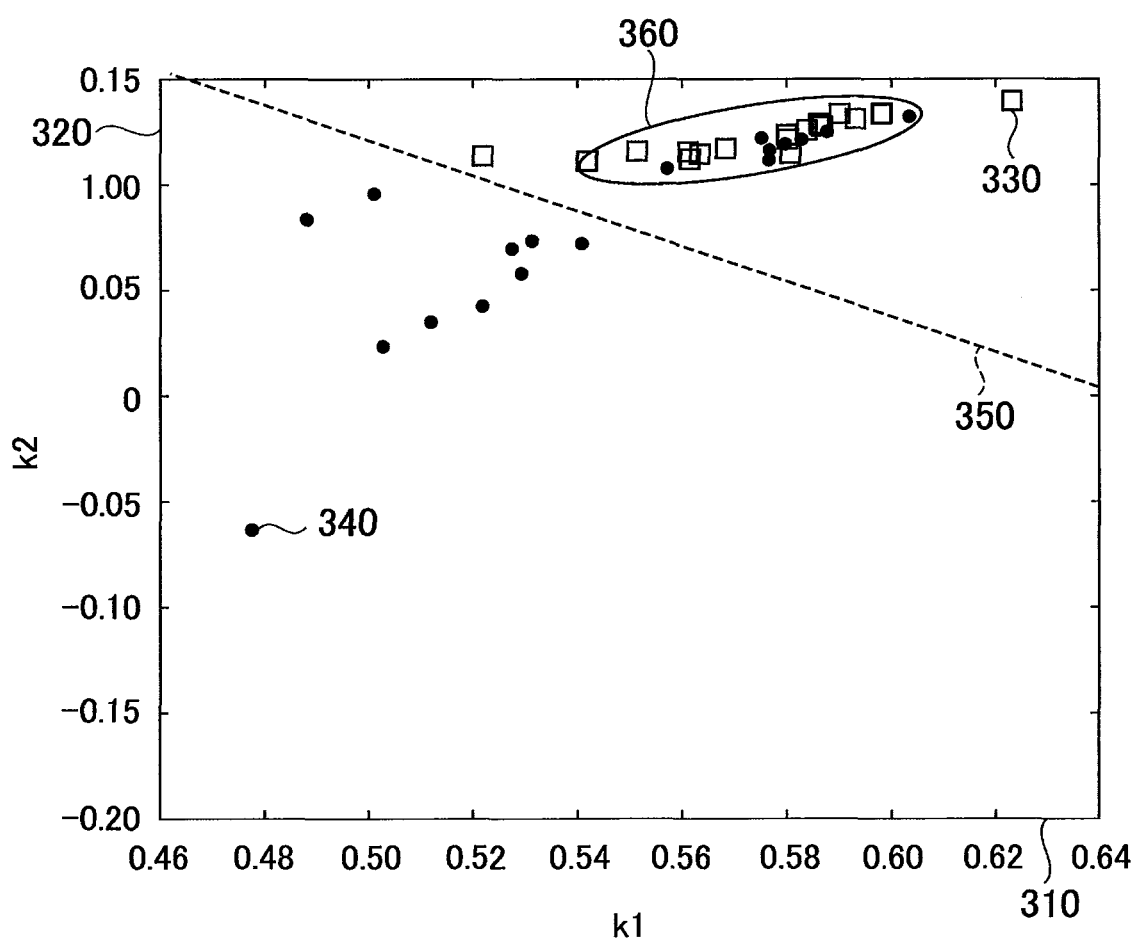
FIG. 8 is a graph showing distributions of approximate expression parameters calculated according to the present invention.

In step S30, it is determined whether there is an abnormality based on the parameter value of the approximate expression calculated in step S25. An abnormality is determined to be present, when, for example, a parameter value is obtained that falls outside a distribution of parameter values of normal data acquired in advance. For example, FIG. 8 shows distributions of parameters $k_1$ and $k_2$ approximated with (expression 4) using normally measured data and data measured with an abnormality existing in mixing conditions. An abscissa 310 represents $k_1$ values and an ordinate 320 represents $k_2$ values. A symbol 330 represents a parameter value obtained from absorbance data under normal mixing conditions and a symbol 340 represents a parameter value obtained from absorbance data under abnormal mixing conditions. An ellipse 360 schematically indicates a rough distribution range of parameter values obtained from absorbance data under the normal mixing conditions. A mixing abnormality may be determined, when the parameter value obtained from measured absorbance falls outside this distribution range.

To determine whether a parameter value obtained from absorbance falls outside the normal distribution, Mahalanobis distance is measured, for example, between the parameter calculated in step S25 and the parameter value distribution of data measured under normal condition. An abnormality can be determined when the distance is equal to, or more than, a predetermined value. This is, however, not the only possible method for determining in step S30 of this present invention. For example, conditions for determining an abnormality are established that includes a threshold value of each parameter value and an abnormality may be determined when the conditions are met for a number of parameter values. Alternatively, a neural network may be set up and used for determining presence of an abnormality from parameter values.

Further, in step S30, an abnormality may be determined by using both a parameter distribution of approximated values corresponding to data measured as normal data and a parameter distribution corresponding to data measured under abnormal condition. In this case, a parameter distribution of normal data and a parameter distribution of abnormal data are found using, for example, data measured under normal condition and data measured under abnormal condition that are previously collected and an identification boundary is formed in a parameter space in order to distinguish normal data parameters from abnormal data parameters. In the distribution shown in FIG. 8, a broken line 350, for example, is defined as the identification boundary. A determination is made to be normal or abnormal based on whichever area, which is separated by the identification boundary, the parameter calculated in step S25 falls. Various existing pattern recognition techniques, such as the multivariate analysis and the neural network, may be applied to the method for establishing the identification boundary.

Alternatively, the cause of the abnormality may be estimated by collecting abnormal data in advance, the causes of which are identified. For example, a parameter distribution of normal data, a parameter distribution of data under abnormal mixing condition, and a parameter distribution of data under deteriorated reagent condition are found in advance. It is then examined whichever parameter distribution the parameter calculated in step S25 is close to. When the parameter is the closest to the parameter distribution of data under abnormal mixing condition, the cause can then be estimated to be abnormal mixing. When the parameter is the closest to the parameter distribution of data under deteriorated reagent condition, the cause can then be estimated to be deteriorated reagent. Although the deteriorated reagent and the abnormal mixing are here cited as examples, various other abnormality causes can be similarly estimated. Additionally, for the method of determining whichever parameter distribution the parameter is the closest to, various existing pattern recognition techniques, such as the multivariate analysis and the neural network, may be applied.

In step S35, a result of determination made in step S30 is output. Various methods are possible for outputting the determination result, variable according to the specific type of abnormality involved in measurement to be detected.

Figure 9:
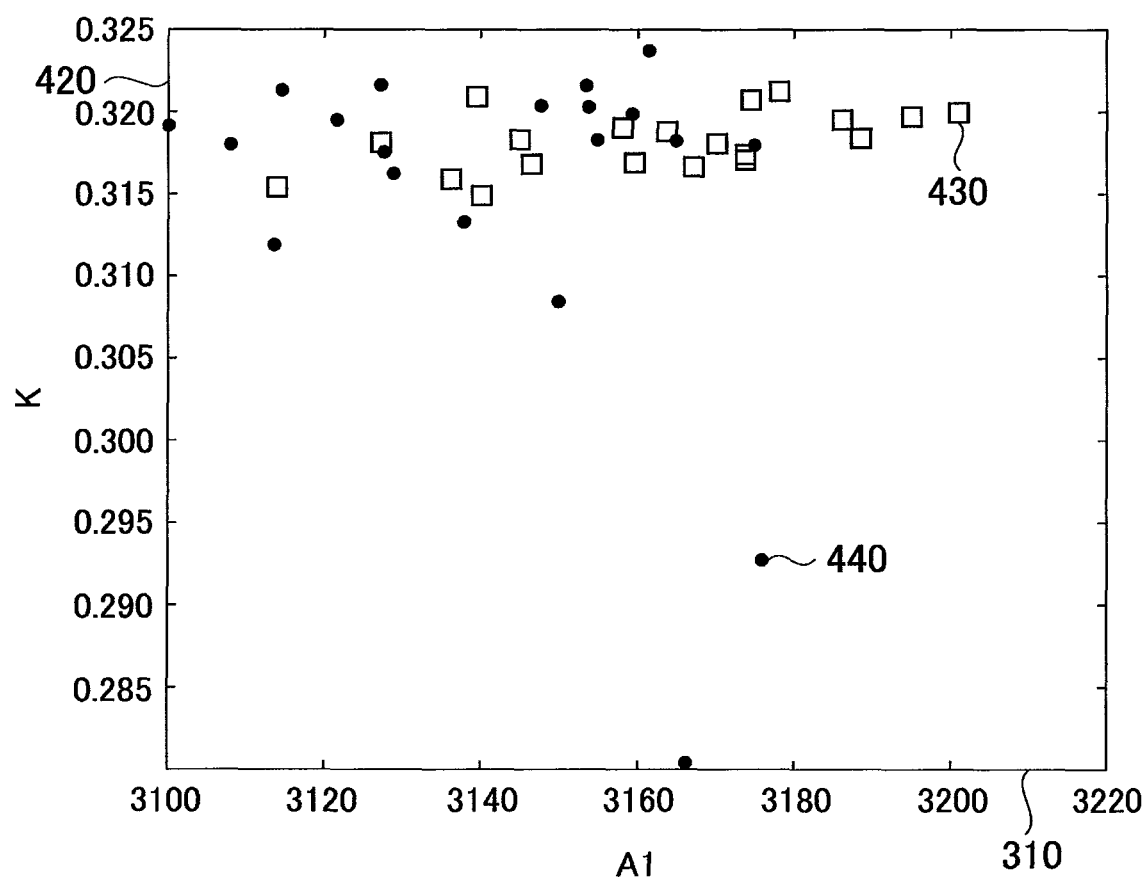
FIG. 9 is a graph showing distributions of approximate expression parameters calculated according to the related art.

FIG. 9 shows a result of parameter distributions examined by approximating, using (expression 1) of the related art, the same absorbance data under the normal mixing conditions and absorbance data under the abnormal mixing conditions as that used in FIG. 8. An abscissa 410 represents A1 values and an ordinate 420 represents k values. A symbol 430 represents a parameter value obtained from absorbance data under normal mixing conditions and a symbol 440 represents a parameter value obtained from absorbance data under abnormal mixing conditions. As is evident from a comparison made with FIG. 7, application of the present invention makes clearer isolation of the parameter values of abnormal data from the parameter values of normal data, enabling detection of abnormalities with higher accuracy than with the related art.

The first embodiment of the present invention described heretofore can be used in daily operation of the automatic analyzer in the following manners.

(1) Evaluating Performance of the Mixing Mechanism Using Daily Test Data

The parameter value of the approximate expression is calculated from the reaction processes in daily test data, quality control sample data, and patient specimen data. The parameter value is stored and daily parameter values are monitored. When an abnormality is detected based on the parameter value, the mixing mechanism, for example, can be identified to be probably defective. The present invention thus enables performance management of, for example, the mixing mechanism from the change with time in the parameter value, thereby contributing to maintenance of apparatus performance.

(2) Detecting a Deteriorated Reagent

The present invention allows reactivity of a reagent to be evaluated by monitoring the approximate expression parameter from results of quality control samples and from patient specimen data in daily test. If a user of the apparatus inadvertently mixes a different reagent or dilutes the reagent in the reagent bottle, a sluggish reaction results, so that the present invention can detect the sluggish reaction as a deteriorated reagent. Approximate expression calculation parameters associated with daily routine items are recorded in the apparatus. If deviation from a predetermined numerical value of an approximate expression calculation parameter is noted in a test, a reagent deterioration is detected, so that an alarm can be issued to notify the user of the apparatus of the reagent deterioration detected. Instead of predetermined numerical values, threshold values may be automatically established from the approximate expression calculation parameters associated with various items for several days.

(3) Recording Reagent Lot Changes

If the user of the apparatus replenishes the supply of a reagent picked from a lot different from a previous one, the present invention can detect different reactivity of the reagent using the approximate expression parameter. Calibration needs to be performed when reagent lots are changed in order to ensure calculation of a correct measured value. The apparatus to which the present invention is applied can automatically detect changes of the reagent lot and, if the calibration is not performed, issues an alarm to thereby prompt a calibration, thus preventing an erroneous measured value from being calculated. Reagent lot changes and calibration performance are recorded in the storage section of the apparatus. Formerly, the user of the apparatus keeps a list external to the apparatus to manage information on reagent lot changes. However, when the apparatus incorporates the functionality according to the present invention, the apparatus detects reagent lot changes. The record of the detected reagent lot changes may be used to recognize frequency of reagent use and aid in ordering reagents or identifying an inventory status of reagents.

(4) Evaluating Reactivity of Reagents

When candidates for reagents to be purchased are to be examined, the present invention calculates, in terms of a single item, approximate expression parameters from a plurality of types of reagents, which permits reactivity evaluation based on the parameter values. In developing reagents, reagents can also be evaluated from the approximate expression parameter values in terms of reactivity, so that criteria can be established for reactive and stable reagents.

(5) Index for Quality Control

The present invention allows an approximate expression parameter to be calculated based on reaction processes of a standard solution and a control in each of various measurement items and monitoring thereof to serve as a quality control sample index.

(6) Method of Evaluating a Mixing Level for Characteristics of Each Reagent

The evaluation method according to the present invention allows an optimum mixing level to be examined for characteristics of each reach in each of various measurement items.

(7) Detecting a Reagent Diluted with Reagent Probe Rinsing Water

Measured values only are not effective in checking for a sluggish reaction that is caused by a diluted reagent and it is difficult to note that the measured values are on a high side. During routine work, it is difficult for a clinical laboratory technologist to visually check reaction processes of all tests. Especially when a measured value is within a normal value range, a sluggish reaction may be overlooked, so that results are of poor accuracy. In the present invention, if the reagent is diluted with reagent probe rinsing water, the sluggish pace of reaction can be evaluated using numerical values of approximate expression calculation parameters derived from the reaction processes. Since the reaction condition can be identified by displaying an evaluated value of the sluggish pace of reaction together with the measured values, accurate results can be reported. Being able to detect sluggish reactions permits the following functions:

Quantitative evaluation of deteriorated reagents
Detection of reagent dilution with rinsing water
Detection of inadvertent mixing of another reagent by the user of the apparatus (8) Assuring Reliability of Test Data Because of the evaluation made using the reaction process of each test data, the approximate expression calculation parameter can be an evaluation value of a certainty factor of a normal reaction for measurements of an analyzed patient specimen. If, for example, a current measured value differs from a preceding measured value of an item in measurement of a patient specimen by using a biochemical automatic analyzer, the laboratory technologist determines whether re-test is necessary based on an examination of other related items and reaction processes thereof. In this case, when the value of the approximate expression calculation parameter falls within a normal reaction distribution, this fact serves as one index for justifying a report that no re-test is necessary and that there is no problem in reactivity of the sample and specimen.

Second Embodiment

A biochemical automatic analyzer according to a second embodiment of the present invention is configured in the same manner as in the first embodiment, as shown schematically in FIG. 2. Except for the control section 13, operation of the automatic analyzer according to the second embodiment of the present invention is the same as that of the first embodiment and detailed descriptions will be omitted.

Figure 10:
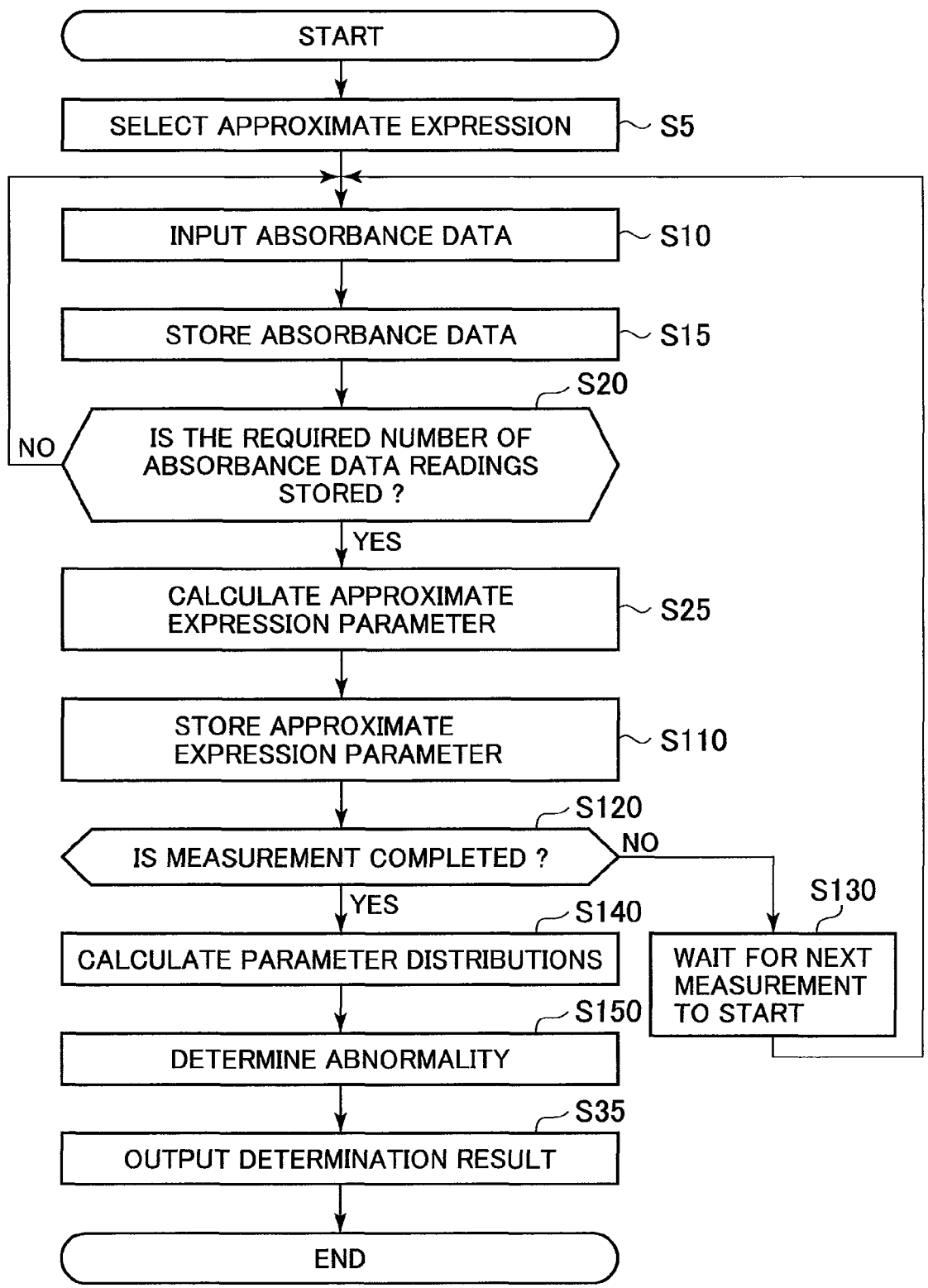
FIG. 10 is a flow chart showing processes performed according to a second embodiment of the present invention.

Processes for determining, from absorbance, whether there is an abnormality according to the second embodiment will be described in detail with reference to FIG. 10. Like or corresponding processes are identified by the same reference numerals as those used in FIG. 1 and detailed descriptions for those processes will be omitted.

Processes of from steps S5 to S25 are the same as those in the first embodiment. In step S110, the parameter value of the approximate expression calculated in step S25 is stored. In this embodiment, a measurement is taken a plurality of times for a specific sample, such as a quality control sample. In step S120, it is determined whether the measurement is taken the plurality of times for the same specific sample. For example, a predetermined plurality of times is set in advance for which the measurement is to be taken and it is then determined whether the measurement is taken for the set plurality of times. When the measurement is completed, control is passed onto step S140. When the measurement is yet to be completed, control waits for the next measurement to start in step S130; when the measurement is started, the control is passed onto step S10 in which an input of absorbance data for the next measurement is started.

In step S140, a distribution of the parameter value stored in step S110 is found. Specifically, for example, a mean value, dispersion, and covariance are obtained. A histogram may be calculated.

In step S150, it is determined whether there is an abnormality based on the numeric value obtained in step S140. To determine whether there is an abnormality, for example, with the apparatus in normal operating conditions, a measurement is taken a plurality of times for the same sample to find approximate expression parameter values and a distribution of the parameter values is stored. The distribution of parameter values obtained in step S140 is compared with the distribution of parameter values stored. When the distributions are identical to each other, it is then determined that there is no abnormality and, when the distributions are different from each other, it is then determined that there is an abnormality. The test technique in statistics may be used to determine whether the distributions are different from each other. Alternatively, a threshold value may be set for the mean value or dispersion of the parameters and the determination is made according to whether the distribution is greater or smaller than the threshold value.

Further, distributions of parameter values for the same sample are obtained and stored in advance with the apparatus in an abnormal condition. A determination is then made as to whether there is an abnormality by determining whether the distribution of the parameter values obtained in step S140 is close to the normal or abnormal distribution. Alternatively, parameter distributions of a plurality of abnormal conditions of known causes of the abnormalities are stored in advance and it may then be determined whichever distribution the distribution of the parameter values obtained in step S140 is the closest to. When the closest distribution is the abnormal distribution, then the cause of the abnormality that yields the distribution is determined to be the estimated cause of the abnormality.

In the present invention, an inspection of, for example, the mixing mechanism upon delivery can be quantitatively performed. A predetermined sample is measured and a reaction process is obtained for a plurality of test items. An approximate expression in the reaction process obtained is calculated to thereby calculate the calculation parameter. A measurement is taken a plurality of times using a similar reagent and sample to check for variations with respect to the numeric value of the calculation parameter. The mixing mechanism can be checked for performance through a comparison made with a predetermined reference value. Not only variations in the measured value, but also variations and the magnitude of the approximate expression parameter value serve as a reference for determining whether normal mixing is performed. A former situation is such that whether mixing is performed or not cannot be determined and, for want of criteria, reproducibility is evaluated only vaguely. The present invention enables quantitative evaluation of, for example, whether mixing is performed and differences in mixing levels.

Additionally, in daily operation of the apparatus, the measurement is taken a plurality of times for the same quality control sample and the like, which permits accurate detection of whether there is an abnormality.

Third Embodiment

The third embodiment is identical to the first embodiment in terms of the configuration shown in FIG. 2 and the process steps shown in FIG. 1, except for the approximate expression selected in step S5 and the approximate expression parameter calculation method in step S25. The steps of these two processes will be described in detail.

In the first embodiment, expressions that represent absorbance x as a function of time t are used for the expressions that can be selected in step S5. In this embodiment, a differential equation is used as the expression. Differential equations are very often used for theoretically illustrating the change in absorbance with time and a theoretical expression can be directly used in this embodiment. For example, let t denote time, x denote absorbance, $\Sigma\{\ \}$ denote a symbol representing a sum of all values, each value being obtained by substituting i in { } for a value of 1 to n, n denote a whole number of 1 or more, fi(t, x) denote a function including t, x, or a time derivative of any order of x, including a constant, and qi denote a parameter. Then, a differential equation of a format expressed by the following expression can be used.

$$\Sigma\{qi*fi(t,x)\}=0 \qquad \text{(Expression 7)}$$

In step S25, a value of the parameter included in (expression 7) is determined using the stored absorbance data. Absorbance is stored as time-series data, so that the time derivative can be calculated by calculating a difference. A value corresponding to fi(t, x) in (expression 7) at the time t at which the absorbance is measured can therefore be obtained. Given values of these at a plurality of time points, (expression 7) can be expressed in a linearly-combined format of fi(t, x) for each, so that the value of parameter qi can be easily obtained through the least squares method. As an example, a case will be described in which the change in absorbance x with time is expressed by an expression given in (expression 8). (Expression 8) corresponds to (expression 7) in which f0(t, x)=1, f1(t, x)=x(t), f2(t, x)=x[1] (t), and f3(t, x)=x[2](t). Where, x[1](t) and x[2](t) represent a first-order time derivative and a second-order time derivative, respectively, of x(t).

$$q0+q1*x(t)+q2*x[1](1)+q3*x[2](t)=0 \qquad \text{(Expression 8)}$$

(Expression 8) may be transformed into a format of (expression 9), when x(t) is the left-hand side and the remaining terms of (expression 8) are the right-hand side.

$$x(t)=r0+r1*x[1](t)+r2*x[2](t) \qquad \text{(Expression 9)}$$

Following assume that absorbance is measured m+1 times to obtain absorbance of x0 to xm. In this case, as a quantity corresponding to the first-order time derivative, m−1 difference values of x′ to x′(m−1) are obtained, for example, through calculations of x′1=(x2−x0)/(2*h) and x′2=(x3−x1)/(2*h). Further, as a quantity corresponding to the second-order time derivative, m−1 difference values of x″1 to x″(m−1) are obtained, for example, through calculations of x″1=(x2−2*×1+x0)/h^2 and x″2=(x3−2*×2+x1)/h^2. Where, h denotes measuring time intervals of absorbance and ^ denotes a power. When xi, x′i, and x″i are substituted for x(t), x[1] (t), and x[2] (t) in (expression 9), (expression 9) can be expressed by (expression 10). Where, i=1 to m−1.

$$xi=r0+r1*x'i+r2*x''i \qquad \text{(Expression 10)}$$

In reality, a relationship expressed by (expression 10) does not match exactly with absorbance observed, so that, in (expression 10), a value of the right-hand side does not match with a value of the left-hand side. Parameters r0, r1, r2 are therefore established using the least squares method so that a difference between the right-hand side and the left-hand side is minimal. Now, let X denote a vector formed by arranging xi vertically, A denote an (m−1)-by-3 matrix shown below, and R=(r0, r1, r2)′. Then, the relationship expressed by (expression 10) is expressed by (expression 11). Where, a symbol ′ denotes transposition.

$$\begin{matrix} 1 & x'1 & x''1 \\ 1 & x'2 & x''2 \\ 1 & x'3 & x''3 \\ \vdots & \vdots & \vdots \\ 1 & x'(m-1) & x''(m-1) \end{matrix} \qquad \text{(Expression 11)}$$

$$X = AR$$

A least squares solution can be obtained with (expression 12) by solving a characteristic equation of (expression 11). Where, inv( ) denotes an inverse matrix of the matrix in ( ).

$$R=\{inv(A'A)\}A'X \qquad \text{(Expression 12)}$$

As described above, in the third embodiment, a differential equation is used as the expression representing the change in absorbance with time, so that a differential equation derived from chemical kinetics can be directly applied. Another effect that can be achieved is to facilitate calculation of the least squares method to determine parameters as compared with the approach in which the absorbance is expressed as a function of time t.

INDUSTRIAL APPLICABILITY

As described in the first to third embodiments, the automatic analyzer to which the present invention is applied can check abnormalities of the apparatus from daily test data in a greater number of test items than the related art, thus contributing to maintenance of performance of the apparatus.

DESCRIPTION OF REFERENCE NUMERALS

1: Sample disk
2: Reagent disk
3: Reaction disk
4: Reaction tank
5: Sampling mechanism
6: Pipetting mechanism
7: Mixing mechanism
8: Photometry mechanism
9: Rinsing mechanism
10: Display section
11: Input section
12: Storage section
13: Control section
14: Piezoelectric element driver
15: Mixing mechanism controller
16: Sample vessel
17, 19: Circular disk
18: Reagent bottle
20: Cool box
21: Reaction vessel
22: Reaction vessel holder
23: Drive mechanism
24, 27: Probe
25, 28: Bearing shaft
26, 29: Arm
31: Fixing section
32: Electrode
33: Nozzle
34: Vertical drive mechanism
110: Axis representing elapsed time
120: Axis representing absorbance
140: Symbol representing absorbance measured at each time point
150: Curve representing absorbance calculated with an approximate expression
220: Axis representing errors between absorbance measured and absorbance calculated with an approximate expression
230: Curve representing errors between absorbance measured and absorbance calculated with (expression 1) used as the approximate expression
240: Curve representing errors between absorbance measured and absorbance calculated with (expression 2) used as the approximate expression
250: Curve representing errors between absorbance measured and absorbance calculated with (expression 4) used as the approximate expression
310: Axis representing values of parameter $k_1$ of (expression 4)
320: Axis representing values of parameter $k_2$ of (expression 4)
330: Symbol representing values of approximate expression parameters k and $k_2$ under normal mixing conditions
340: Symbol representing values of approximate expression parameters $k_1$ and $k_2$ under abnormal mixing conditions
350: Example of a straight line for distinguishing between approximate expression parameters under normal mixing conditions and approximate expression parameters under abnormal mixing conditions
360: Distribution range of approximate expression parameters under normal mixing conditions
410: Axis representing parameter A1 values of (expression 1)
420: Axis representing parameter k values of (expression 1)
430: Symbol representing values of approximate expression parameters A1 and k under normal mixing conditions
440: Symbol representing values of approximate expression parameters A1 and k under abnormal mixing conditions

The invention claimed is:

1. An automatic analyzer comprising:
a sample disk holding a plurality of sample vessels;
a reaction disk holding a plurality of reaction vessels;
a reagent disk;
a storage mechanism for storing approximate expressions for changes in measured values with time, each of the approximate expressions being associated with a corresponding test item or specimen;
a multiwavelength photometer configured to detect absorbance data of a reaction in a reaction vessel of the plurality of reaction vessels, the absorbance data stored as a plurality of measured values for one of the test items or specimens at a plurality of measurement points in time;
a parameter optimizing mechanism for calculating parameter values of one of the approximate expressions associated with the one of the test items or specimens stored in the storage mechanism based on the measured values; and
a determining mechanism for determining whether an abnormality is present in the measured values based on the parameter values optimized by the parameter optimizing mechanism,
wherein the one of the approximate expressions is:

$$x = a_0 + a_1 * \exp(-k_1 * t) + a_2 * \exp(-k_2 * t),$$

where t denotes a measurement point in time, x denotes a calculated value, and * denotes multiplication,
parameter values $a_0$, $a_1$, $a_2$, $k_1$ and $k_2$ in the one of the approximate expressions are optimized so that a difference between the measured values and the calculated values obtained with the one of the approximate expressions at the measurement points in time are minimized, and
the determining mechanism determines the presence of the abnormality in the measured values when the parameter values fall outside a predetermined range, and issues a notification of the presence of the abnormality in the measured values for the one of the test items or specimens.

2. The automatic analyzer according to claim 1, wherein:
a first-order or a second-or-higher-order time derivative of the one of the approximate expressions is calculated;
parameter values p and $p_i$ are calculated so that an expression:

$$p + S\{p_i * x[n](t)\} = 0 \text{ holds, where}$$

t denotes a measurement point in time, x denotes a calculated value, x[n](t) denotes a nth-order time derivative of the measured value at time t, S{ } denotes a symbol representing a sum of all values, each value being obtained by substituting i in { } for a value of 0 to n, n denotes a whole number, and * denotes multiplication; and
the presence of the abnormality is determined based on the parameter values.

3. The automatic analyzer according to claim 1, wherein:
a first-order or a second-or-higher-order time derivative of the one of the approximate expressions is calculated;
parameter values $q_i$ are calculated so that an expression:

$$S\{q_i * f_i(t,x)\} = 0 \text{ holds, where}$$

t denotes a measurement point in time, x denotes a calculated value, S{ } denotes a symbol representing a sum of all values, each value being obtained by substituting i in { } for a value of 0 to n, n denotes a whole number of 1 or more, $f_i(t, x)$ denotes a function including t, x, or a time derivative of any order of x, * denotes multiplication, and $f_i(t, x)$ may include a constant; and the presence of the abnormality is determined based on the parameter values.

4. The automatic analyzer according to claim 1, wherein:

the determining mechanism determines the presence of the abnormality by comparing the parameter values optimized by the parameter optimizing mechanism with a distribution of parameters obtained under normal conditions.

5. The automatic analyzer according to claim 1, wherein:

the determining mechanism determines the presence of the abnormality by comparing the parameter values optimized by the parameter optimizing mechanism with both a distribution of parameter values obtained under normal conditions and a distribution of parameter values obtained under abnormal conditions.

6. The automatic analyzer according to claim 1, wherein:

the determining mechanism includes an abnormality cause estimating mechanism for estimating a cause of the determined abnormality by comparing the parameter values optimized by the parameter optimizing mechanism with distributions of parameter values obtained under abnormal conditions where causes of the abnormal conditions have been previously identified.

7. An automatic analyzer comprising:

a sample disk holding a plurality of sample vessels;

a reaction disk holding a plurality of reaction vessels;

a reagent disk;

a storage mechanism for storing approximate expressions for changes in measured values with time, each of the approximate expressions being associated with a corresponding test item or specimen;

a multiwavelength photometer configured to detect absorbance data of a reaction in a reaction vessel of the plurality of reaction vessels, the absorbance data stored as a plurality of measured values for one of the test items or specimens at a plurality of measurement points in time;

a parameter optimizing mechanism for calculating parameter values of one of the approximate expressions associated with the one of the test items or specimens stored in the storage mechanism based on the measured values; and a determining mechanism for determining whether an abnormality is present in the measured values based on the parameter values optimized by the parameter optimizing mechanism, wherein the one of the approximate expressions is:

$$x = a_0 + S\{a_i * \exp(-k_i * t)\},$$

where t denotes a measurement point in time, x denotes a calculated value, S{ } denotes a symbol representing a sum of all values, each value being obtained by substituting i in { } for a value of 1 to n, n denotes a whole number of 1 or more, and * denotes multiplication, parameter values $a_0$, $a_i$ and $k_i$ in the one of the approximate expressions are optimized so that a difference between the measured values and the calculated values obtained with the one of the approximate expressions at the measurement points in time are minimized, and the determining mechanism determines the presence of the abnormality in the measured values when the parameter values fall outside a predetermined range, and issues a notification of the presence of the abnormality in the measured values for the one of the test items or specimens.

8. An automatic analyzer comprising:

a sample disk holding a plurality of sample vessels;

a reaction disk holding a plurality of reaction vessels;

a reagent disk;

a storage mechanism for storing approximate expressions for changes in measured values with time, each of the approximate expressions being associated with a corresponding test item or specimen;

a multiwavelength photometer configured to detect absorbance data of a reaction in a reaction vessel of the plurality of reaction vessels, the absorbance data stored as a plurality of values for one of the test items or specimens at a plurality of measurement points in time;

a parameter optimizing mechanism for calculating parameter values of one of the approximate expressions associated with the one of the test items or specimens stored in the storage mechanism based on the measured values; and a determining mechanism for determining whether an abnormality is present in the measured values based on the parameter values optimized by the parameter optimizing mechanism, wherein one of the approximate expressions is:

$$x = a_0 + S[n]\{a_i * \exp(-k_i * t)\} + S[m]\{b_i/(c_i + d_i * t)\} + S[l]\{p_i/(\exp(q_i * t) + r_i)\},$$

where t denotes a measurement point in time, x denotes a calculated value, S[n]{ } denotes a symbol representing a sum of all values, each value being obtained by substituting i in { } for a value of 1 to n, S[m]{ } denotes a symbol representing a sum of all values, each value being obtained by substituting i in { } for a value of 1 to m, S[l]{ } denotes a symbol representing a sum of all values, each value being obtained by substituting i in { } for a value of 1 to n, where n, m, and l denote whole numbers of 1 or more, and * denotes multiplication, parameter values $a_0$, $a_i$, $k_i$, $b_i$, $c_i$, $d_i$, $p_i$, $q_i$, $r_i$ in the one of the approximate expressions are optimized so that a difference between the measured values and the calculated values obtained with the one of the approximate expressions at the measurement points in time are minimized, and the determining mechanism determines the presence of the abnormality in the measured values when the parameter values fall outside a predetermined range, and issues a notification of the presence of the abnormality in the measured values for the one of the test items or specimens.

9. An analysis method of an automatic analyzer including a sample disk holding a plurality of sample vessels; a reaction disk holding a plurality of reaction vessels; a reagent disk, the method comprising the steps of:

storing approximate expressions for changes in measured values with time, each of the approximate expressions being associated with a corresponding test item or specimen;

measuring, by a multiwavelength photometer, absorbance data of a reaction in a reaction vessel of the plurality of reaction vessels, the absorbance data stored as a plurality of measured values with a measurement device for one of the test items or specimens at a plurality of measurement points in time;

optimizing parameters of one of the approximate expressions associated with the one of test items or specimens based on the measured values;

determining whether an abnormality is present in the measured values when the optimized parameters fall outside a predetermined range; and issuing a notification of the presence of the abnormality in the measured values for the one of the test items or specimens.

10. An analysis method of an automatic analyzer including a sample disk holding a plurality of sample vessels; a reaction disk holding a plurality of reaction vessels; a reagent disk, the method comprising the steps of:

storing approximate expressions for changes in measured values with time, each of the approximate expressions being associated with a corresponding test item or specimen;

measuring, by a multiwavelength photometer, absorbance data of a reaction in a reaction vessel of the plurality of reaction vessels, the absorbance data stored as a plurality of values with a measurement device for one of the test items or specimens at a plurality of measurement points in time;

optimizing parameters of one of the approximate expressions associated with the one of test items or specimens based on the measured values;

determining whether an abnormality is present in the measured values when the optimized parameters fall outside a predetermined range;

when an abnormality is determined to be present in the measured values, estimating a cause of the abnormality by comparing the optimized parameters with distributions of parameter values obtained under abnormal conditions where causes of the abnormal conditions have been previously identified; and issuing a notification of the cause of the presence of the abnormality in the measured values for the one of the test items or specimens.

* * * * *